(12) United States Patent
Boettcher et al.

(10) Patent No.: US 10,058,487 B2
(45) Date of Patent: Aug. 28, 2018

(54) POLYMERIZABLE DENTAL MATERIAL

(71) Applicant: Muhlbauer Technology GmbH, Hamburg (DE)

(72) Inventors: Henrik Boettcher, Tostedt (DE); Stephan Neffgen, Pinneberg (DE)

(73) Assignee: Muhlbauer Technology GmbH, Hamburg (DE)

( * ) Notice: Subject to any disclaimer, the term of this patent is extended or adjusted under 35 U.S.C. 154(b) by 0 days.

(21) Appl. No.: 15/120,372

(22) PCT Filed: Feb. 17, 2015

(86) PCT No.: PCT/EP2015/053303
§ 371 (c)(1),
(2) Date: Aug. 19, 2016

(87) PCT Pub. No.: WO2015/124559
PCT Pub. Date: Aug. 27, 2015

(65) Prior Publication Data
US 2017/0065496 A1    Mar. 9, 2017

(30) Foreign Application Priority Data
Feb. 21, 2014  (DE) .......... 10 2014 203 166

(51) Int. Cl.
*A61K 6/083*   (2006.01)
*A61K 6/00*    (2006.01)

(52) U.S. Cl.
CPC ............ *A61K 6/0052* (2013.01); *A61K 6/083* (2013.01)

(58) Field of Classification Search
None
See application file for complete search history.

(56) References Cited

U.S. PATENT DOCUMENTS

| | | | | | |
|---|---|---|---|---|---|
| 3,541,068 | A | * | 11/1970 | Taylor | C08F 20/16 260/998.11 |
| 6,084,004 | A | * | 7/2000 | Weinmann | A61K 6/0017 522/100 |
| 6,620,864 | B2 | * | 9/2003 | Schmid | A61K 6/087 433/226 |
| 2002/0040103 | A1 | * | 4/2002 | Schmid | A61K 6/087 525/107 |
| 2004/0067323 | A1 | * | 4/2004 | Clabburn | G03F 7/001 428/1.26 |
| 2006/0004122 | A1 | * | 1/2006 | Hecht | C09J 4/00 523/115 |
| 2006/0052470 | A1 | * | 3/2006 | Grech | A61K 6/083 522/6 |
| 2011/0275035 | A1 | * | 11/2011 | Lu | A61K 6/083 433/216 |

FOREIGN PATENT DOCUMENTS

| | | |
|---|---|---|
| DE | 19848886 | 5/2000 |
| EP | 2153811 | 2/2010 |
| WO | WO 2000/049064 | 8/2000 |
| WO | WO 2011/139936 | 11/2011 |

OTHER PUBLICATIONS

Structure Search, 15120372-549348, Aug. 24, 2017 (Year: 2017).*
Allen et al., Photochemistry and photo-induced co-synergistic polymerisation activities of novel N,N,-dimethylaminobenzoates and benzamides. Journal of Photochemistry and Photobiology A: Chemistry. 2000;137(2-3):169-176.
International Search Report and Written Opinion for PCT/EP2015/053303, dated May 7, 2015, 11 pages.

* cited by examiner

*Primary Examiner* — Peter A Salamon
(74) *Attorney, Agent, or Firm* — Casimir Jones, S.C.; Mary Ann D. Brow

(57) ABSTRACT

The invention relates to a dental material, which contains: at least one monomer, containing at least one radically polymerizable ehtylenically unsaturated group and at least one acid group; at least one monomer, which contains no acid groups and at least one radically polymerizable ethylenically unsaturated group; at least one photoinitiator; and at least one tertiary aromatic amine as a coinitiator, which amine has a benzene ring, to which at least one dialkylamine group and at least one further group are directly bonded. According to the invention, the further group is selected from carboxylic acid ester groups containing at least one polyoxyalkylene group having at least 2 oxyethylene and/or oxypropylene units; and amide groups.

21 Claims, No Drawings

POLYMERIZABLE DENTAL MATERIAL

The present application is a § 371 US National Entry of International Application No. PCT/EP2015/053303, filed Feb. 17, 2015, which claims the benefit of German Application No. 10 2014 203 166.4, filed Feb. 21, 2014.

The invention relates to a polymerizable dental material according to the generic term of claim 1. An additional subject-matter of the invention is the use of a tertiary aromatic amine as claimed in claim 13 as coinitiator in a polymerizable dental material. Another subject-matter of the invention is a coinitiator with improved water solubility, and also a radically polymerizable dental restoration material comprising the coinitiator, the bond strength of which on the tooth, with the simplest application, is improved. The radically polymerizable dental material is preferably a flowable, self-etching and self-bonding composite for direct fillings.

Particular demands are placed on dental restoration materials. This applies in particular for direct filling materials, fixing cements or adhesives which will comprise a polymerizable acid as adhesive and/or etching component, applied intraorally and light-cured.

The dental restoration materials must be completely harmless biologically and toxicologically and must exhibit the highest possible depth of cure (DOC), a low polymerization shrinkage, a high storage stability (2 or more years, preferably at ambient temperature) and low sensitivity to ambient light, as well as, in the cured state, the desired light opaqueness, colour stability, radio-opacity, a low water uptake (WU) and water solubility (WS), and also the highest possible flexural strength (FS). The polymerized restoration should in particular exhibit the highest possible shear bond strength (SBS) on dentine.

In particular, it is known, in order to increase the SBS of restoration materials on dentine, to add higher proportions of polymerizable acids to dental restoration materials.

The presence of a proportion of hydrophilic monomers (water solubility >50 g/l) not comprising any acid group is also preferred. Those hydrophilic monomers which are miscible with water in any proportion are preferred; mention may be made here of 2-hydroxyethyl methacrylate (HEMA) in particular.

The polymerization shrinkage and the strength of dental restoration materials can be improved by addition of known crosslinking agents and inorganic fillers. Use is preferably made, as crosslinking agent, of mixtures of di(meth)acrylate based on bisphenol A and a low molecular weight crosslinking agent, such as triethylene glycol dimethacrylate (TEDMA). Suitable inorganic fillers exhibit particle sizes of less than 30 μm and a hydrophobized surface. Use is preferably made, as inorganic fillers, of radiopaque silanized glasses.

Well known self-bonding and self-etching radically polymerizable dental restoration materials, in particular flowable composites for direct filling, exhibit a need for improvement with regard to the abovementioned properties. In particular, an additional need exists to improve the SBS of flowable composites on dentine, without the dentine being preprepared with separate etchants and/or separate bonding agents.

Well known light-curing, self-bonding and self-etching radically polymerizable dental restoration materials comprise a photoinitiator and a tertiary aromatic amine as coinitiator. A combination of camphorquinone and/or phosphine oxide compounds as photoinitiators and also alkyl 4-dialkylaminobenzoates or butoxyethyl 4-dialkylaminobenzoates as coinitiators is particularly preferred. Such materials have been described many times; mention may be made here, by way of example, of the following documents: WO2011139936, EP 2 286 784, EP 2 153 811, WO2007100569, EP 1 784 155, EP 1 387 657 and EP 0 136 186.

A cationically curable dental restoration material is described in WO 00/49064, which restoration material should comprise ω-ethylpoly(oxyethylene) 4-[bis(ω-(2-hydroxyethyl)poly(oxyethylene))amino]benzoate (PEG-25-PBA) as coinitiator. However, this coinitiator is described therein as disadvantageous in comparison with the alkyl 4-dialkylaminobenzoates, since it exhibits only a low reactivity.

It is an object of the present invention to make available an improved dental material for direct tooth restoration which exhibits a high DOC and also a high SBS and FS of the cured restoration material. The simultaneous maintenance or improvement in properties such as complete biological and toxicological harmlessness, storage stability, insensitivity to ambient light and polymerization shrinkage, and also colour stability, low water uptake (WU) and water solubility (WS) in the cured state, is preferred.

The invention achieves this object through the characteristics of the independent patent claims. Advantageous embodiments are given in the dependent patent claims.

The subject-matter of the invention is a dental material, in particular a light-curing, self-bonding and self-etching radically polymerizable dental restoration material, which comprises:

a. at least one monomer comprising at least one radically polymerizable ethylenically unsaturated group and at least one acid group, b. at least one monomer not comprising any acid groups and comprising at least one radically polymerizable ethylenically unsaturated group, c. at least one photoinitiator, d. at least one tertiary aromatic amine as coinitiator, which amine exhibits a benzene ring to which at least one dialkylamine group and at least one additional group are directly bonded, characterized in that the additional group is chosen from:
  i. carboxylic acid ester groups comprising at least one polyoxyalkylene group with at least 2 oxyethylene and/or oxypropylene units, and
  ii. amide groups.

The invention makes available a dental material, preferably a dental adhesive, with the properties mentioned in the problem definition, which is to be applied simply and safely with few processing stages. Preferably, the bonding surface (the dentine) does not have to be prepared beforehand with etchants and bonding agents. The term "polymerizable dental material" describes, in the context of the invention, any dental material, the curing of which at least in substantial parts is carried out by (preferably radical) polymerization and which can be used for a or in a dental restoration. Preferably, a dental material according to the invention exhibits at least one, more preferably two, more preferably all three, of the following properties: light-curing, self-bonding and self-etching. A restoration material or an adhesive may be concerned.

An attempt to explain the action of the invention, to which the Applicant Company is not committed, is that the improved bonding to dentine and the good mechanical properties of the dental material according to the invention (with high reactivity) are based on increased amphiphilicity of the coinitiator, which, on the one hand, brings about a very good solubility in an aqueous hybrid layer of the dentine as also in the dental material itself, the dental material itself being comparatively hydrophobic.

The invention has recognized that high proportions of polymerizable acids and HEMA according to the state of the art in a dental restoration material have various disadvantages; in particular, they can reduce the depth of cure (DOC) and can increase the water uptake (WU) and water solubility (WS) so much that the restorations are no longer completely harmless biologically and toxicologically. Furthermore, it is difficult, with such compositions, to achieve the desired flexural strength of the restoration material.

The preferred radically polymerizable ethylenically unsaturated groups are the acrylate, the methacrylate, the acrylamide and the methacrylamide group. (Meth)acryl always subsequently stands for both acryl and methacryl.

Suitable polymerizable acids according to characteristic group (a), i.e. monomers comprising at least one radically polymerizable ethylenically unsaturated group and at least one acid group, are well known to a person skilled in the art.

Preferred acid groups are the carboxylic acid, phosphoric acid, phosphonic acid, bisphosphonic acid and sulphonic acid groups. Phosphorus-comprising acid groups are particularly preferred.

Mention may be made, by way of example, of: 4-[(meth) acryloyloxyethyl]trimellitic acid; bis[2-(meth)acryloyloxyethyl]phosphate; 10-(meth)acryloyloxydecyl dihydrogen phosphate (MDP); or 2-acrylamido-2-methylpropanesulphonic acid.

In the dental material, the polymerizable acid (a) is preferably present at 1% to 20% by weight, more preferably at 1% to 15% by weight and particularly preferably at 5% to 15% by weight, based on the total weight of the monomers comprising at least one radically polymerizable ethylenically unsaturated group present in the dental material.

In the dental material, the photoinitiator (c) is preferably present at 0.05% to 10% by weight, preferably at 0.05% to 5% by weight and most preferably at 0.1% to 2% by weight, based on the total weight of the monomers comprising at least one radically polymerizable ethylenically unsaturated group present in the dental material.

Preferred photoinitiators (c) intensely absorb light in the wavelength range between 390 and 560 nm, particularly preferably between 420 and 480 nm. The photoinitiator is preferably an aliphatic 1,2-diketone which is soluble in the dental material, such as camphorquinone (CQ) or propyl phenyl diketone (PPD), particularly preferably however camphorquinone and/or a camphorquinone derivative for example exhibiting a carboxyl, carboxylate, sulphonic acid or sulphonate group. The light absorption in the given range triggers an initiating transformation which leads to radical formation in the photoinitiator system.

The tertiary aromatic amine (coinitiator according to characteristic group (d)) is preferably chosen from the group consisting of:

a)

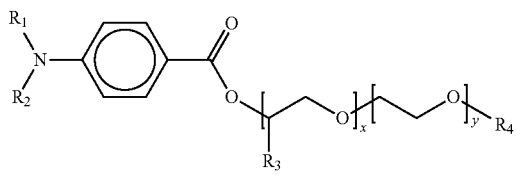

Formula I b)

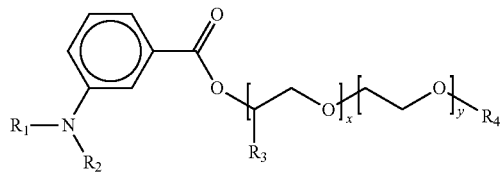

Formula II c)

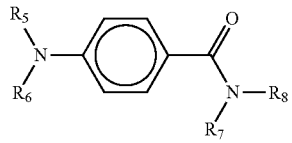

Formula III d)

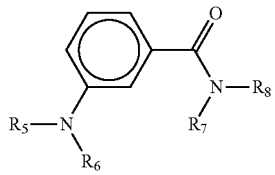

Formula IV in which, in the formulae represented:
$R_1$ and $R_2$ are, independently of one another, $C_1$-$C_5$-alkyl, preferably methyl,
$R_3$ is alkyl, preferably methyl,
$R_4$ is H or $C_1$-$C_5$-alkyl, preferably methyl,
$R_5$ and $R_6$ are, independently of one another, $C_1$-$C_5$-alkyl, preferably methyl,
$R_7$ and $R_8$ are, independently of one another, chosen from H, alkyl, alkoxyalkyl and polyalkylene oxide, preferably polyalkylene oxide with at least two oxyethylene and/or oxypropylene units,
$x \geq 0$ and $y > 1$.

The sum of x and y preferably amounts to from 3 to 20, more preferably from 5 to 17. Preferably, $x < y$.

For the coinitiators (d) of the formulae I and II, the polyalkylene oxide chains can be formed as block copolymers or as statistical copolymers. A polyalkylene oxide chain preferably has a molar mass between 130 and 1200 g/mol, more preferably between 220 and 1200 g/mol, more preferably between 300 and 800 g/mol. An example is polyethylene glycol 350 monomethyl ether 4-dimethylaminobenzoic acid ester.

Suitable coinitiators (d) of the formulae III and IV are 4-dimethylaminobenzamide; 4-dimethylamino-N-propylbenzamide; 3-dimethylamino-N-propylbenzamide; 4-dimethylamino-N-(hydroxyethyl)benzamide; 4-dimethylamino-N-(hydroxypropyl)benzamide; 4-dimethylamino-N-(hydroxybutyl)benzamide; 4-dimethylamino-N-(2-methoxyethyl)benzamide; 3-dimethylamino-N-(2-methoxyethyl)benzamide; 4-dimethylamino-N-(2-(2-hydroxyethoxy)ethyl)benzamide. Particularly suitable coinitiators (d) of the formulae III and IV are 4-dimethylamino-N-(2-(2-(2-methoxyethoxy)ethoxy)ethyl)benzamide; 4-dimethylamino-N-(polyethylene oxide methyl ether)benzamide; 4-dimethylamino-N-(poly(propylene oxide-block-ethylene oxide) methyl ether)benzamide; 4-dimethylamino-N-(poly(ethylene oxide-stat-propylene oxide) methyl ether) benzamide.

The polyalkylene oxide chains can be used as block copolymers or also as statistical copolymers. A polyalkylene oxide chain has particularly preferably a molar mass between 130 and 1200 g/mol.

The coinitiators according to the invention without an amide group exhibit a water solubility >2 g/l, more preferably >50 g/l, more preferably >100 g/l, more preferably >500 g/l.

The coinitiators according to the invention with an amide group exhibit a water solubility >0.4 g/l, preferably >2 g/l, more preferably >50 g/l, more preferably >100 g/l, more preferably >500 g/l.

In the dental material, the coinitiator (d) is present at 0.05% to 10% by weight, preferably at 0.1% to 10% by weight and most preferably at 0.5% to 5% by weight, based on the total weight of the monomers comprising at least one radically polymerizable ethylenically unsaturated group present in the dental material.

Suitable additional monomers (b), i.e. monomers comprising at least one radically polymerizable ethylenically unsaturated group not exhibiting any acid group, are well known to a person skilled in the art.

Preferably, the at least one monomer not comprising any acid groups and comprising at least one radically polymerizable ethylenically unsaturated group (characteristic b) of claim 1) is chosen from the group consisting of b1), b2) and b3), with:

b1)

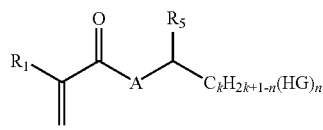

in which, in the formula represented:
$R_1$ is H, methyl or ethyl, preferably H or methyl;
A is O or $NR_3$ with $R_3$=H, methyl, ethyl or propyl; preferably $R_3$=H;
HG is a hydrophilic group chosen from OH and (O—$CH_2$—$CH_2$)$_m$—$OR_4$; preferably HG=OH;
$R_5$ is H, methyl, ethyl or $C_kH_{2k+1-n}(HG)_n$, preferably H;
$R_4$ is H or methyl;
k, m and n are natural numbers;
k=1-5, preferably 1-2;
m=3-20, preferably 5-20;
n=1-5;
n≤k;
each carbon atom carries at most one hydrophilic group HG;
b2) $(QAE_v)_rC_tH_{(2t+2)-(r+s)}(HG)_s$
with

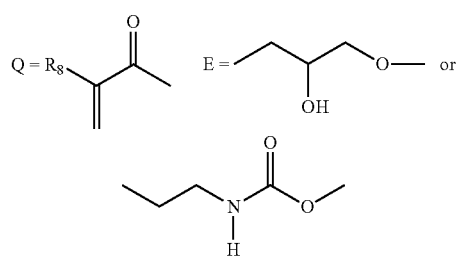

in which, in the formulae represented:
$R_8$ is H, methyl or ethyl, preferably H or methyl;
A is O or $NR_3$, with $R_3$=H, methyl, ethyl or propyl; preferably $R_3$=H;
HG is OH or (O—$CH_2$—$CH_2$)$_m$—$OR_7$, preferably OH;
$R_7$ is H or methyl;
m, r, s, t and v are natural numbers;
m=3-20, preferably 6-20;
r=2-4;
s=1-4;
t=2-8, preferably 2-6;
v=0 or 1, preferably 0;
b3) Q-A-$E_v$-$C_2H_2$-HG-$E_v$-A-Q
with

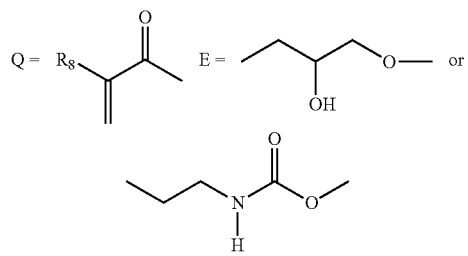

in which, in the formulae represented:
$R_8$ is H, methyl or ethyl, preferably H or methyl;
A is O or $NR_3$, with $R_3$=H, methyl, ethyl or propyl; preferably $R_3$=H;
HG is (O—$CH_2$—$CH_2$)$_m$;
m=4-20, preferably 6-20;
v=0 or 1, preferably 0.

Preferred monomers b1) as described above are well known to a person skilled in the art. Examples are hydroxyethyl methacrylate, hydroxypropyl methacrylate, hydroxyethylacrylamide, hydroxypropylacrylamide, 2,3-dihydroxypropyl methacrylate, 1,3-dihydroxy-2-propyl methacrylate, methoxy(polyethylene glycol 350) methacrylate or methoxy (polyethylene glycol 500) methacrylate. Hydroxyethyl methacrylate (HEMA) is particularly preferred.

Preferred monomers b2) as described above are well known to a person skilled in the art. Examples are glycerol dimethacrylate and N,N"-(1,2-dihydroxyethylene)bisacrylamide. Additional preferred monomers are described in EP 2 133 368 (Sekiguchi).

Preferred monomers b3) as described above are well known to a person skilled in the art. Examples are polyethylene glycol 200 di(meth)acrylate; polyethylene glycol 300 di(meth)acrylate; polyethylene glycol 400 di(meth)acrylate; polyethylene glycol 600 di(meth)acrylate; PPGDMA, polypropylene glycol dimethacrylate.

Suitable monomers b1) to b3) preferably exhibit at least a water solubility of 50 g/l of water.

The dental material according to the invention can preferably exhibit, in addition, at least one monomer b4) not comprising any acid groups and comprising at least two radically polymerizable ethylenically unsaturated groups, this at least one monomer b4) not being chosen from the group b1), b2) and b3).

Preferred monomers b4) as described above are well known to a person skilled in the art. Examples are allyl (meth)acrylate; 1,3-propanediol di(meth)acrylate; 1,3-butanediol di(meth)acrylate; 1,4-butanediol di(meth)acrylate; 1,5-pentanediol di(meth)acrylate; neopentyl glycol di(meth)acrylate; 1,6-hexanediol dimethacrylate; 1,9-nonanediol di(meth)acrylate; 1,10-decanediol di(meth)acrylate; 1,12- dodecanediol di(meth)acrylate; ethyleneglycol di(meth)acrylate; diethylene glycol di(meth)acrylate; triethylene glycol di(meth)acrylate; tetraethylene glycol di(meth)acrylate; neopentyl glycol propoxylate (2) di(meth)acrylate; bisphenol A di(meth)acrylate; bisphenol A glycerolate di(meth)acrylate (BisGMA); bisphenol A ethoxylate di(meth)acrylate; bisphenol A propoxylate di(meth)acrylate; diurethane di(meth)acrylate (UDMA); tricyclo[5.2.1.0]decanedimethanol di(meth)acrylate; N,N'-ethylenebisacrylamide; N,N'-diethyl(1,3-propylene)bisacrylamide; N,N'-(2,2,4-trimethylhexamethylene)bismethacrylamide; bis[2-(2-methylacryloylamino)ethoxycarbonyl] hexamethylenediamine; trimethylolpropane tri(meth)acrylate; ditrimethylolpropane tetra(meth)acrylate; dipentaerythritol penta(meth)acrylate; dipentaerythritol hexa(meth)acrylate.

The water solubility of the monomer b4) preferably amounts to less than 50 g/l.

Mixtures of at least one monomer b1) to b3) and at least one monomer or crosslinking agent from the group b4) are particularly preferred.

The dental material which can be radically polymerized by exposure to visible light furthermore comprises preferably 0.1% to 90% by weight, preferably 45% to 70% by weight, of organic and/or inorganic fillers.

Suitable fillers are well known to a person skilled in the art. Surface-treated inorganic fillers, which in comparison with the acids of a resin matrix are essentially inert, e.g. which are insoluble in the dental material, i.e. the resin matrix, the term "resin matrix" being understood to mean the radically polymerizable monomers and additives dissolved therein, are preferred. Suitable fillers are revealed, for example, in EP 1 720 506 (Neffgen et al.).

The dental material which can be polymerized radically by exposure to visible light further comprises preferably from 0.01% to 20% by weight, preferably from 0.01% to 10% by weight, of normal dental additives.

The choice of the additives is taken by a person skilled in the art depending on the planned use of the dental material. Normal dental additives are polymerization inhibitors, such as BHT, UV stabilizers, rheology modifiers, colourants and radiopaque compounds.

The dental material which can be polymerized radically by exposure to visible light can furthermore comprise non-polymerizable organic solvents, for example readily volatile solvents, such as ethanol or acetone, and also water.

A further subject-matter of the invention is a composition according to the invention for use as a light-curing, self-bonding and self-etching radically polymerizable dental restoration material or the use of such a composition as or in the preparation of a light-curing, self-bonding and self-etching radically polymerizable dental restoration material.

An additional subject-matter of the invention is the use of a tertiary aromatic amine which exhibits a benzene ring to which at least one dialkylamine group and at least one additional group are directly bonded, the additional group being chosen from:
  i. carboxylic acid ester groups comprising at least one polyoxyalkylene group with at least 2 oxyethylene and/or oxypropylene units, and
  ii. amide groups,
    as coinitiator in a light-curing, self-bonding and self-etching radically polymerizable dental restoration material.

Exemplary embodiments of the invention are illustrated below.

Materials Used:

| | |
|---|---|
| 10-Methacryloyloxydecyl dihydrogen phosphate (MDP) | PCM Products |
| 2-(2-Aminoethoxy)ethanol | Alfa Aeser |
| 2,6-Di(tert-butyl)-4-methylphenol (BHT) | Merck |
| 2-Hydroxyethyl methacrylate (HEMA) | Melrob (Evonik) |
| 2-Methoxyethylamine | Merck |
| 3-Dimethylaminobenzoic acid | Merck |
| 3-Trimethoxysilylpropyl methacrylate (MEMO) | Evonik |
| 4-Dimethylaminobenzoic acid | Alfa Aeser |
| 2-Ethylhexyl 4-dimethylaminobenzoate (EHA) | Rahn |
| Ethyl 4-dimethylaminobenzoate | Sigma Aldrich |
| 2-(n-Butoxy)ethyl 4-dimethylaminobenzoate | |
| 4-Dimethylaminobenzonitrile | Alfa Aeser |
| 4-Dimethylaminobenzoyl chloride | Alfa Aeser |
| Active charcoal | Merck |
| $Al_2O_3$ TLC sheets (Polygram Alox N/UV$_{254}$) | Macherey-Nagel |
| $Al_2O_3$ for column chromatography (aluminium oxide 90 active, neutral) | Merck |
| $BaCO_3$ | Sigma Aldrich |
| Bisphenol A diglycidyl dimethacrylate (BisGMA) | CCP Composites |
| $CaCl_2$, anhydrous | Sigma Aldrich |
| Camphor-10-sulphonic acid | Merck |
| Celite 545 | Merck |
| $CuSO_4 \cdot 5H_2O$ | Merck |
| D,L-Camphorquinone (CQ) | Rahn |
| Dibenzo-18-crown-6 | Sigma Aldrich |
| Dichloromethane | Merck |
| Diethyl ether | Carl Roth |
| Dimethyl sulphoxide | Merck |
| Dowex 50 WX 8 | Fluka |
| Acetic acid | Merck |
| Ethanol | Walter CMP |
| Ethyl acetate | Merck |
| Ethyldiisopropylamine | Acros |
| Glass powder BAF GM 27884 0.7 μm, silanized with 3-trimethoxysilylpropyl methacrylate | Schott |
| $H_2O_2$, 35% | Sigma Aldrich |
| HCl | Merck |
| Hydrophobic highly dispersed silica (HDK 2000) | Wacker |
| Jeffamine M 1000 | Huntsman |
| $K_2CO_3$ | J. T. Baker |
| $K_3PO_4$ | Alfa Aeser |
| Methanol | Sigma Aldrich |
| $Na_2S_2O_5$ | Sigma Aldrich |
| $Na_2O_3$ | Merck |
| $Na_2SO_4$ | Merck |
| $NaBH_4$ | Merck |
| NaCl | Merck |
| $NaHCO_3$ | J. T. Baker |
| $NaN_3$ | Merck |
| NaOH | Merck |
| Sodium ethoxide solution, 21% in ethanol | Sigma Aldrich |
| n-Heptane | Merck |
| n-Propylamine | Sigma Aldrich |
| O-(Benzotriazol-1-yl)-N,N,N',N'-tetramethyluronium tetrafluoroborate (TBTU) | Iris Biotech |
| Polyethylene glycol monomethyl ether 350 | Sigma Aldrich |
| p-Toluenesulphonyl chloride | Fluka |
| Sulphuric acid | Sigma Aldrich |
| Selenium dioxide | Merck |
| $SiO_2$ TLC sheets (Polygram Sil G/UV$_{254}$) | Macherey-Nagel |
| $SiO_2$ for medium-pressure chromatography (Silica gel 60, 0.04-0.063 mm) | Merck |
| $SiO_2$ for column chromatography (Silica gel 60, 0.063-0.200 mm) | Merck |
| Tetrahydrofuran (THF) | Sigma Aldrich |
| Tetrahydrofuran (THF), anhydrous | Sigma Aldrich |
| Toluene | Merck |
| Triethylene glycol dimethacrylate (TEDMA) | Lehmann & Voss |
| Triethylene glycol monomethyl ether | Merck |
| Deionized water | DMG |

Syntheses

Camphorquinone-10-sulphonic acid 3.15 g (28.4 mmol) of selenium dioxide are dissolved in 20 ml of deionized water in a one-necked flask with a magnetic stirrer bar. 10.6 g (45.6 mmol) of camphor-10-sulphonic acid are added thereto and the flask is provided with a reflux condenser. The reaction mixture is heated to 110° C. under reflux. Three additional portions of selenium dioxide, each of 3.15 g, are added to the batch at intervals of 3 h. After the final addition, heating is carried out at 110° C. under reflux for 4.5 h. After cooling to ambient temperature, the batch is filtered through Celite 545 and the filter residue is washed with 2×50 ml of deionized water. The solution is diluted with an additional 50 ml of deionized water, and also mixed with 2 ml of a 20% sulphuric acid solution, and transferred into a two-necked flask.

In a gas-generating apparatus, sulphur dioxide is generated from 63 g of $Na_2SO_3$ and 100 ml of 6M $H_2SO_4$ inside an hour and led through a capillary into the filtered batch. The reddish brown batch is stirred overnight after gas introduction has ended. The gas generation and introduction described above is then repeated. The reddish brown-black batch is filtered through Celite 545 and the filter residue is washed with deionized water. Approximately 130 ml of water are distilled off from the batch at 100 mbar. The distillation residue is neutralized with solid $BaCO_3$. The viscous reddish brown mass is filtered through Celite 545 and the filter residue is washed with approximately 150 ml of deionized water. A clear yellow solution is obtained. The solution is concentrated on a rotary evaporator until approximately 80 ml of liquid remain. In this connection, a white precipitate is produced and is filtered off. The clear yellow solution is added to a column (h=12 cm, d=2 cm) with ion exchanger (Dowex 50WX8, H-form). After the solution has completely soaked into the column, the column is rinsed with deionized water until the liquid exiting from the column is colourless. The yellow solution is concentrated to dryness on a rotary evaporator and the residue is dried under vacuum at ambient temperature. The crude product (approximately 10.9 g) is dissolved in 100 ml of methanol. Approximately 2 g of active charcoal are added to the solution and the suspension is heated under reflux for two hours. After cooling to ambient temperature, filtration through Celite 545 is carried out and the filter residue is washed with 3×20 ml of methanol. A clear light-yellow solution is obtained. Methanol is removed on a rotary evaporator. After drying under vacuum, a highly viscous light-yellow liquid remains, which liquid crystallizes overnight in a refrigerator. The yellow solid is recrystallized from ethyl acetate/n-heptane. Yield: 6.02 g. $^1$H NMR ($d_6$-DMSO) ppm: 0.82 (s, 3H), 0.11 (s, 3H), 1.50 (m, 1H), 1.65 (m, 1H), 2.13 (m, 1H), 2.59 (d, 1H), 2.65 (d, 1H), 2.75 (dt, 1H), 2.95 (d, 1H), melting point: 155° C. Approximately 10% of the starting material, camphor-10-sulphonic acid, is present as impurity.

Sodium camphorquinone-10-sulphonate 1.01 g (4.1 mmol) of the camphorquinone-10-sulphonic acid are dissolved in 0.5 ml of deionized water. The solution is cooled in an ice bath. 2 ml of a 2N NaOH solution are slowly added dropwise using an Eppendorf pipette. The ice bath is removed and the solution is stirred at ambient temperature for three hours. The water is distilled off on a rotary evaporator. The residue is dried over $CaCl_2$ under vacuum. The product is obtained as a yellow solid. Yield: 0.99 g, melting point: 250° C. (decomposition).

Polyethylene glycol monomethyl ether 4-dimethylaminobenzoate 35 g of polyethylene glycol monomethyl ether (100 mmol) and 29 g (150 mmol) of ethyl 4-dimethylaminobenzoate are added to a two-necked flask with a magnetic stirrer bar. 2 ml of a sodium ethoxide solution (21% by weight in ethanol (5 mmol)) are added thereto. The flask is closed with a stopcock and stopper and the contents are placed under vacuum (750 mbar). The flask is suspended in a preheated oil bath (100° C.) and the vacuum is adjusted down stepwise to 40 mbar. After two hours, the vacuum is broken and the batch is cooled down to approximately 50° C. 2 ml of the sodium ethoxide solution (5 mmol in ethanol) are then once again added. A low vacuum of 750 mbar is again applied and the flask is transferred into a 100° C.-warm oil bath. The vacuum is then reduced stepwise to 40 mbar and the batch is left under these conditions in the oil bath for three hours. The batch is then brought to ambient temperature and the vacuum is broken. For the workup, the batch is added to a mixture of 500 ml of deionized water and 5 ml of a 2N HCl solution. A white precipitate is formed. The solid is filtered off. 1 ml of a saturated sodium bisulphite solution is added to the filtrate and the pH is adjusted to approximately 7.5 with a 2N NaOH solution. The yellowish green emulsion is provided with 6.3 g of active charcoal and shaken for one hour on a vibrating plate. The suspension is filtered through Celite 545. The aqueous solution is extracted with 3×150 ml of dichloromethane. The organic phase is dried over $Na_2SO_4$. The dehydrating agent is separated and the solvent is removed on a rotary evaporator. After drying under vacuum, the product is obtained as a slightly yellowish oil. Yield: 28.2 g, $^1$H NMR ($CDCl_3$) ppm: 3.00 (s, 6H), 3.35 (s, 3H), 3.52 (t, 2H), 3.56-3.75 (br, approximately 30H), 3.79 (t, 2H), 4.39 (t, 2H), 6.61 (d, 2H), 7.89 (d, 2H).

Triethylene glycol monomethyl ether 4-dimethylaminobenzoate 0.92 g (5 mmol) of 4-dimethylaminobenzoyl chloride, 20 ml of anhydrous THF and 1.16 ml (7 mmol) of diisopropylethylamine are introduced at ambient temperature into a one-necked flask with a magnetic stirrer bar, dropping funnel and $CaCl_2$ drying tube. The solution is cooled in an ice bath to 0° C. A solution of 5 ml of anhydrous THF and 0.78 ml (4.9 mmol) of triethylene glycol monomethyl ether is prepared in the dropping funnel. This solution is slowly added dropwise to the reaction batch while cooling with ice. After the addition, the batch is allowed to come to ambient temperature. The batch is stirred at ambient temperature for approximately 70 h with the exclusion of moisture and light. Some precipitate is produced in this connection. For the workup, the solution is poured off from the precipitate. The precipitate is washed with some THF. The organic phases are combined and the solvent is removed on a rotary evaporator. The residue is taken up in 50 ml of dichloromethane. The organic phase is extracted by shaking with 2×10 ml of 0.5N HCl solution, 1×10 ml of saturated $NaHCO_3$ solution and 1×10 ml of saturated NaCl solution. The organic phase is subsequently dried over $Na_2SO_4$. After filtration, the solvent is removed on a rotary evaporator and the residue is dried under high vacuum. 1.47 g of crude product are obtained. The crude product is further purified by column chromatography. Stationary phase: $SiO_2$. Eluent: ethyl acetate/n-heptane 1:1. Column: h=35 cm, d=4 cm. The product has an $R_f$=0.17. The product is obtained as a clear pale-yellow oil. Yield: 0.75 g. $^1$H NMR (CDCl$_3$) ppm: 3.00 (s, 6H), 3.34 (s, 3H), 3.50 (m, 2H), 3.60-3.70 (br, approximately 6H), 3.78 (t, 2H), 4.39 (t, 2H), 6.60 (d, 2H), 7.89 (d, 2H).

4-Dimethylaminobenzamide 2.31 g (15.8 mmol) of recrystallized 4-dimethylbenzonitrile are dissolved in 10 ml of DMSO in a two-necked flask with a magnetic stirrer bar, dropping funnel and reflux condenser. 0.32 g (2.3 mmol) of K$_2$CO$_3$ are added to the light-brown solution. 1.9 ml of a 35% H$_2$O$_2$ solution (18.6 mmol in water) are slowly added dropwise at ambient temperature inside 5 min. A white solid precipitates in the course of this. After the addition, stirring is carried out at ambient temperature under reflux for a further 45 min. During this phase, the temperature briefly rises. So much white solid is formed that the magnetic stirrer bar no longer moves. For the workup, 50 ml of deionized water are added to the batch and the mush is homogenized with a spatula. The solid is separated via a sintered glass funnel and washed with 3×20 ml of deionized water. The solid is dried in a desiccator under vacuum at ambient temperature over CaCl$_2$. The product is obtained as a white solid. Yield: 2.42 g. $^1$H NMR (d$_6$-DMSO) ppm: 2.95 (s, 6H), 6.67 (d, 2H), 6.89 (br. s, NH), 7.60 (br. s, NH), 7.73 (d, 2H).

4-Dimethylamino-N-(poly(propylene oxide-block-ethylene oxide) methyl ether)benzamide 4.25 g (20 mmol) of anhydrous K$_3$PO$_4$, ground in a pestle and mortar, are introduced into a three-necked flask with a magnetic stirrer bar, a dropping funnel, a reflux condenser and a stopcock. The flask is flushed with nitrogen and the entire apparatus is heated with a hot air gun. Cooling is carried out to ambient temperature in the N$_2$ flow. 80 ml of anhydrous THF are then added to the K$_3$PO$_4$. 2.94 g (16 mmol) of 4-dimethylaminobenzoyl chloride and 0.04 g (0.1 mmol) of dibenzo-18-crown-6 are added to the suspension. A solution of 8.04 g of Jeffamine M 1000 in 12 ml of anhydrous THF is prepared and transferred to the dropping funnel. The Jeffamine M 1000 solution is added to the batch at ambient temperature inside 15 min with the exclusion of moisture. A balloon, filled with N$_2$, is then fixed to the apparatus. During the day, the batch is heated in an oil bath at 50° C. for 5 to 8 h under protective gas and reflux. Stirring is carried out at ambient temperature for the remaining time. In total, the batch is stirred at 50° C. for 44 h and at ambient temperature for 148 h. For the workup, the batch is filtered. The filter residue is washed with some THF. The solvent is removed on a rotary evaporator and the residue is freed from volatile components under high vacuum. The crude product is added to a mixture of 80 ml of deionized water and 0.8 ml of 2N HCl. The emulsion formed is again diluted with 100 ml of deionized water and filtered. 0.5 ml of saturated sodium bisulphite solution is added to the filtered solution and the pH is adjusted to 7.5 with 2N NaOH. The aqueous phase is extracted in a separating funnel with 3×60 ml of dichloromethane. The combined organic phases are dried over Na$_2$SO$_4$. Solid NaCl is added to the extracted aqueous phase, whereupon an organic phase settles out. This is separated and likewise dried over Na$_2$SO$_4$. All the dried organic phases are combined and the solvent is removed under vacuum on a rotary evaporator. The product is obtained as a light beige waxy solid. Yield: 5.94 g. $^1$H NMR (CDCl$_3$) ppm: 1.04 (m, approximately 5H), 1.17 (m, approximately 3H), 1.76 (m, approximately 1H), 2.93 (s, 6H), 3.29 (s, approximately 3H), 3.31-3.51 (br, approximately 10H), 3.56 (s, approximately 78H), 6.34 (d, NH), 6.58 (d, approximately 2H), 7.67 (m, approximately 2H).

4-Dimethylamino-N-(2-(2-hydroxyethoxy)ethyl) benzamide 6.61 g (40 mmol) of 4-dimethylaminobenzoic acid were suspended in 200 ml of dichloromethane in a one-necked flask with a magnetic stirrer bar and a stopper and dissolved by addition of 13.22 ml (80 mmol) of ethyldiisopropylamine. 12.85 g (40 mmol) of TBTU were added to the clear solution in portions at ambient temperature. After the end of the addition, the flask was closed with a stopper and stirred at ambient temperature for 14 h. A yellow, slightly cloudy solution was formed. 4 ml (40 mmol) of 2-(2-aminoethoxy) ethanol were dissolved in 100 ml of dichloromethane in a 500 ml four-necked flask with two stoppers, an internal thermometer, a magnetic stirrer bar and a dropping funnel with a CaCl$_2$ drying tube. The solution was cooled to 0° C. with an ice bath. The mixture of 4-dimethylaminobenzoic acid, ethyldiisopropylamine and TBTU in dichloromethane was transferred into the dropping funnel and slowly added, within 90 min, to the 2-(2-aminoethoxy)ethanol solution, the internal temperature not increasing above 5° C. After the end of the addition, the ice bath was removed and the reaction mixture was stirred at ambient temperature for 48 h. For the workup, the reaction mixture was transferred into a separating funnel and extracted with 4×25 ml of 0.5N acetic acid solution, 2×25 ml of saturated NaHCO$_3$ solution and 1×25 ml of saturated NaCl solution. The organic phase was dried over Na$_2$SO$_4$. The solvent was removed on a rotary evaporator. 180 ml of diethyl ether were added to the residue. Not everything dissolved in the course of this. The clear diethyl ether phase was poured off from the solid. The solvent was removed on a rotary evaporator. Yield of crude product: 12.12 g. For additional purification, the crude product was dissolved in 70 ml of a 10:2 mixture of ethyl acetate/ethanol. 65 g of Al$_2$O$_3$ were added to this and the solvent mixture was removed on a rotary evaporator. The crude product absorbed on Al$_2$O$_3$ was added to a column (d=3 cm) filled with 100 g of Al$_2$O$_3$ and the crude product was purified by column filtration. Eluent: ethyl acetate/ethanol 10:2. The eluent was removed on a rotary evaporator and the residue was freed from volatile components under vacuum. Yield of purified crude product: 9.24 g.

2-(2-(2-Methoxyethoxy)ethoxy)ethyl tosylate 18.73 g (114 mmol) of methoxytriethylene glycol were introduced into a three-necked flask and dissolved in 60 ml of THF. The solution was cooled to approximately 0° C. using an ice bath. 35 ml of a 6N NaOH solution were added to the solution. The mixture warmed to 8° C. in the course of this. After the internal temperature was again at approximately 0° C., a solution of 40.4 g (212 mmol) of p-toluenesulphonyl chloride in 70 ml of THF was added dropwise to the solution with vigorous stirring, the internal temperature being maintained below 5° C. After the end of the addition, stirring was carried out at approximately 0° C. for 30 min. The ice bath was then removed and the batch was stirred at ambient temperature for 45 min. For the workup, the batch was added to 300 ml of diethyl ether. 50 ml of a 1 NaOH solution were added to this and extraction was carried out. The organic phase was separated and extracted again with 50 ml of a 1N NaOH solution. After renewed separation of the organic phase, this was dried over $Na_2SO_4$ and the solvent was removed on a rotary evaporator. Yield of crude product: 44.91 g.

The crude product was further purified by column chromatography. For this, approximately 5 g were put onto a silica gel column (column: d=3 cm, stationary phase 75 g of $SiO_2$). Elution was first carried out with the eluent mixture n-heptane/ethyl acetate 10:1 (approximately 1.2 l), until no more starting material (p-toluenesulphonyl chloride) could be detected by thin layer chromatography. The eluent mixture was then adjusted to n-heptane/ethyl acetate 1:1 and the product was eluted. The solvent was removed on a rotary evaporator and the residue was freed from volatile components under vacuum. Yield: 4.21 g. $^1$H NMR ($CDCl_3$) ppm: 2.42 (s, 3H), 3.35 (s, 3H), 3.51 (m, 2H), 3.57-3.60 (m, 6H), 3.64-3.67 (t, 2H), 4.11-4.15 (t, 2H), 7.32 (d, 2H), 7.77 (d, 2H).

2-(2-(2-Methoxyethoxy)ethoxy)ethyl azide 0.45 g (6.9 mmol) of $NaN_3$ were suspended in 1 ml of deionized water in a screw-top test tube with a magnetic stirrer bar. A solution of 1.50 g (4.7 mmol) of 2-(2-(2-methoxyethoxy)ethoxy)ethyl tosylate in 0.5 ml of THF was added thereto. The batch was sealed and was heated in an oil bath at 70° C. for 7.5 h with vigorous stirring. For the workup, the batch was added to 15 ml of deionized water and extracted with 4×25 ml of diethyl ether. The organic phase was dried over $Na_2SO_4$ and the solvent was subsequently removed on a rotary evaporator. The residue was freed from volatile components under vacuum. Yield: 0.71 g. $^1$H NMR ($CDCl_3$) ppm: 3.31-3.34 (m, 5H), 3.47-3.50 (m, 2H), 3.58-3.63 (m, 8H).

2-(2-(2-Methoxyethoxy)ethoxy)ethylamine 1.54 g (6.17 mmol) of $CuSO_4.5H_2O$ were dissolved in 180 ml of methanol in a flask. The solution was cooled in an ice bath to 0° C. 0.69 g of $NaBH_4$ was added to the solution with stirring. Vigorous gas generation and a slight warming began and a black suspension was formed. 11.68 g (61.7 mmol) of 2-(2-(2-methoxyethoxy)ethoxy)ethyl azide dissolved in 90 ml of methanol were added to the black suspension. 6×412 mg (6×10.9 mmol) of $NaBH_4$ were added to the batch at 0° C. inside 3.75 h. After the last addition, stirring was carried out at 0° C. for a further 30 min. For the workup, the batch was adjusted to pH=12 with 2N NaOH solution. A precipitate was formed in the course of this, which precipitate was filtered off through a sintered glass funnel with a thin layer of Celite 545. The residue was washed with some methanol. The methanol solution was allowed to stand overnight; some precipitate was formed once more. Methanol was removed on a rotary evaporator and the residue was taken up in 800 ml of dichloromethane. The organic phase was dried over $Na_2SO_4$. The solvent was removed on a rotary evaporator and the residue was removed from volatile components under vacuum. The residue was taken up in 30 ml of toluene, filtered and mixed with an additional 200 ml of toluene. Approximately 70 ml of toluene were distilled off in order to azeotropically dry the crude product. Residual toluene was removed on a rotary evaporator and the residue was freed from volatile components under vacuum. The crude product (8.12 g) was further purified by a distillation in a Kugelrohr. The product distilled over between 160 and 200° C. at 5 mbar as a colourless oil.

Yield: 6.58 g. $^1$H NMR ($CDCl_3$) ppm: 2.82 (t, 2H), 3.33 (s, 3H), 3.47-3.51 (m, 4H), 3.58-3.61 (m, 6H).

4-Dimethylamino-N-(2-(2-(2-methoxyethoxy)ethoxy)ethyl)benzamide 5.43 g (25 mmol) of $K_3PO_4$, which had been finely crushed in a pestle and mortar, were heated with a hot air blower in a two-necked flask with a dropping funnel, a stopcock and a magnetic stirrer bar in a weak $N_2$ flow. Cooling was carried out to ambient temperature under $N_2$ and 100 ml of anhydrous THF were subsequently added. 1.84 g (10 mmol) of 4-dimethylaminobenzoyl chloride and 26 mg (0.07 mmol) of dibenzo-18-crown-6 were weighed out in a weighing dish and added to the batch. 25 ml of anhydrous THF were mixed with 1.63 g (10 mmol) of 2-(2-(2-methoxyethoxy)ethoxy)ethylamine in the dropping funnel. This solution was slowly added dropwise to the batch at ambient temperature under $N_2$. After the end of the addition, a $CaCl_2$ drying tube was put on the batch. The reaction mixture was stirred at ambient temperature for 24 h and subsequently at 60° C. for 2.5 h. For the workup, the batch was filtered through Celite 545 and the filter residue was washed with 20 ml of THF. THF was removed on a rotary evaporator and the residue was taken up in 100 of dichloromethane. The organic phase was extracted with 2×20 ml of 0.5N HCl solution, 1×20 ml of saturated $NaHCO_3$ solution and 1×20 ml of saturated NaCl solution. The organic phase was dried over $Na_2SO_4$ and the solvent was removed on a rotary evaporator. The aqueous wash phases were combined and water was removed on a rotary evaporator. The residue was extracted with 100 ml of acetone and 50 ml of ethanol. The acetone and ethanol extracts were combined and the solvent was removed on a rotary evaporator. Thin layer chromatography ($SiO_2$, eluent ethyl acetate/ethanol 95:5) of the crude product from the dichloromethane phase and from the aqueous phase both showed a product spot at $R_f$=0.22. As a result of this, both crude products were dissolved in dichloromethane and combined, and the solvent was removed on a rotary evaporator. Yield of crude product: 2.53 g. Additional purification was carried out by medium-pressure chromatography. Stationary phase: $SiO_2$. Eluent: ethyl acetate/ethanol 95:5. Flow rate: 40 ml/min. Column: h=46 cm, d=2.6 cm. Yield: 0.8 g. $^1$H NMR ($CDCl_3$) ppm: 2.98 (s, 6h), 3.32 (s, 3H), 3.49-3.52 (m, 2H), 3.61-3.63 (m, 10H), 6.63 (d, 2H), 7.68 (d, 2H).

Synthesis of the 4-dimethylamino-N-propylbenzamide 1.66 g (10 mmol) of 4-dimethylaminobenzoic acid are suspended in 100 ml of dichloromethane in a two-necked flask with a magnetic stirrer bar, stopper, a reflux condenser and a $CaCl_2$ drying tube. 3.37 ml (20 mmol) of diisopropylethylamine are added to the suspension, whereupon a clear solution is produced. 3.22 g (10 mmol) of TBTU (2-(1H-benzotriazol-1-yl)tetramethyluronium tetrafluoroborate) are added portionwise to the solution. A slightly cloudy, yellow solution is formed. This mixture is stirred at ambient temperature for one hour. 1.64 ml (20 mmol) of n-propylamine are then added dropwise with cooling. The batch warms up slightly in the course of this and the colour of the solution lightens. The cooling water is switched off after the end of the addition and the batch is stirred at ambient temperature overnight. In the course of this, a light beige, clear solution is formed.

For the workup, the batch is extracted with 20 ml of a 2N HCl solution. Extraction is subsequently carried out with 20 ml of a saturated NaHCO$_3$ solution. The organic phase is dried over Na$_2$SO$_4$ and filtered, and the solvent is removed on a rotary evaporator. 3.04 g of a slightly greenish-yellow highly viscous liquid are obtained as crude product. The crude product is further purified by column chromatography. Stationary phase: Al$_2$O$_3$, neutral. Eluent: ethyl acetate/n-heptane 1:1. Column: h=50 cm, d=4 cm. The product has an R$_f$=0.3. The pure fractions are combined, the solvent is removed on a rotary evaporator and the residue is dried at ambient temperature under vacuum. The product is obtained as a white solid. Yield: 0.64 g. $^1$H NMR (CDCl$_3$) ppm: 0.98 (t, 3H), 1.63 (sext., 2H), 3.02 (s, 6H), 3.42 (m, 2H), 6.03 (s, 1H), 6.72 (d, 2H), 7.69 (d, 2H).

Synthesis of the
3-dimethylamino-N-propylbenzamide 1.66 g (10 mmol) of 3-dimethylaminobenzoic acid are suspended in 50 ml of dichloromethane in a three-necked flask with a magnetic stirrer bar, a stopper with an internal thermometer, a dropping funnel, a reflux condenser and a CaCl$_2$ drying tube. 3.37 ml (20 mmol) of diisopropylethylamine are added to the suspension, whereupon a light-brown, clear solution is formed. 3.21 g (10 mmol) of TBTU (2-(1H-benzotriazol-1-yl)tetramethyluronium tetrafluoroborate) are added portionwise to the solution. A slightly cloudy, yellow-brown solution is formed. This mixture is stirred at ambient temperature for one hour. A mixture of 10 ml of dichloromethane and 1.64 ml (20 mmol) of n-propylamine is prepared in the dropping funnel. The flask is cooled with an ice/sodium chloride mixture. The mixture is slowly added dropwise from the dropping funnel to the reaction mixture at an internal temperature of approximately 0° C. inside 15 min. The cold bath is removed 10 min after the addition and the batch is stirred at ambient temperature for 72 h. For the workup, approximately 50 g of neutral Al$_2$O$_3$ are added to the batch and the solvent is removed on a rotary evaporator. Additional drying is carried out at ambient temperature under vacuum. The Al$_2$O$_3$ is transferred into a column with a sintered glass plate and eluted with 800 ml of a 1:1 mixture of ethyl acetate/n-heptane. The solvent is removed on a rotary evaporator and the residue is dried at ambient temperature under vacuum. 3.31 g of a yellow, highly viscous liquid are obtained as crude product. The crude product is further purified by column chromatography. Stationary phase: SiO$_2$. Eluent: ethyl acetate/n-heptane 1:1. Column: h=50 cm, d=3 cm. The product has an R$_f$=0.19. The pure fractions are combined, the solvent is removed on a rotary evaporator and the residue is dried at ambient temperature under vacuum. The product is obtained as a clear, slightly yellowish, highly viscous liquid which crystallizes overnight in a refrigerator to give a slightly yellowish solid. Yield: 1.84 g. $^1$H NMR (CDCl$_3$) ppm: 0.98 (t, 3H), 1.63 (sext., 2H), 3.00 (s, 6H), 3.42 (m, 2H), 6.24 (s, 1H), 6.87 (dd, 1H), 7.00 (d, 1H), 7.24-7.30 (br, 2H).

Synthesis of the
4-dimethylamino-N-(2-methoxyethyl)benzamide 1.66 g (10 mmol) of 4-dimethylaminobenzoic acid are suspended in 90 ml of dichloromethane in a three-necked flask with a magnetic stirrer bar, a stopper with an internal thermometer, a dropping funnel, a reflux condenser and a CaCl$_2$ drying tube. 3.37 ml (20 mmol) of diisopropylethylamine are added to the suspension, whereupon a light solution is produced. 3.22 g (10 mmol) of TBTU (2-(1H-benzotriazol-1-yl)tetramethyluronium tetrafluoroborate) are added portionwise to the solution. A clear yellow solution is formed. This mixture is stirred at ambient temperature for one hour. A mixture of 10 ml of dichloromethane and 1.72 ml (20 mmol) of 2-methoxyethylamine is prepared in the dropping funnel. The flask is cooled with an ice/sodium chloride mixture. The mixture is slowly added dropwise from the dropping funnel to the reaction mixture at an internal temperature of approximately 0° C. inside 15 min. Cooling is carried out for a further 20 min and the cold bath is then removed. A clear solution with a white solid is formed. On warming to ambient temperature, the solid redissolves and the solution remains slightly cloudy. Stirring is carried out at ambient temperature for 72 hours. For the workup, approximately 40 g of neutral Al$_2$O$_3$ are added to the batch and the solvent is removed on a rotary evaporator. Additional drying is carried out at ambient temperature under vacuum. The Al$_2$O$_3$ is transferred into a column with a sintered glass plate and eluted with a 1:1 mixture of ethyl acetate/n-heptane. The solvent is removed on a rotary evaporator. 2.90 g of crude product are isolated. Additional purification is carried out by recrystallizing twice from ethyl acetate. The product is obtained as a white solid. Yield: 1.74 g. $^1$H NMR (CDCl$_3$) ppm: 3.02 (s, 6H), 3.38 (s, 3H), 3.54 (t, 2H), 3.63 (m, 2H), 6.44 (s, 1H), 6.73 (d, 2H), 7.71 (m, 2H).

Synthesis of the
3-dimethylamino-N-(2-methoxyethyl)benzamide 3.31 g (20 mmol) of 3-dimethylaminobenzoic acid were suspended in 125 ml of dichloromethane in a three-necked flask with a magnetic stirrer bar, an internal thermometer, a reflux condenser with a CaCl$_2$ drying tube and also a dropping funnel with a stopper. 6.62 ml (40 mmol) of ethyldiisopropylamine were added thereto. A clear slightly brownish solution was formed. 6.43 g (20 mmol) of TBTU were weighed out in a weighing pan and added portionwise at ambient temperature to the batch. A yellow-brown solution was formed. The solution was stirred at ambient temperature for 1 h. The batch was subsequently cooled in an ice bath to 0° C. A mixture of 3.45 ml (40 mmol) of 2-methoxyethylamine in 25 ml of dichloromethane was prepared in the dropping funnel. This solution was added dropwise to the batch inside 35 min, so that the internal temperature did not increase above 3° C. The colour of the reaction mixture lightened and a solid was formed. After the addition had ended, the ice bath was removed and the batch was stirred at ambient temperature for 48 h. For the workup, the reaction mixture was transferred into a separating funnel and extracted with 2×50 ml of 0.5N HCl solution, 1×50 ml of saturated NaHCO$_3$ solution and 1×50 ml of saturated NaCl solution. The organic phase is dried over Na$_2$SO$_4$ and the solvent is removed on a rotary evaporator. Yield of crude product: 2.85 g.

Methods

All investigations and syntheses were carried out at 23±2° C. and standard air pressure, unless expressly indicated otherwise.

A SpeedMixer DAC 150 FV from Hauschild was used for the preparation of pastes. An Exakt 50 three-roll mill from Exakt was used for the homogenization of the pastes. The pastes were degassed under vacuum.

Small amounts of substance were distilled with a Glass Oven B 585 Kugelrohr from Büchi.

Medium-Pressure Chromatography

An MPLC system from Büchi was used. It consisted of a pump module C-601, a pump manager C-615 and a fraction collector C-660. The test samples to be chromatographed were dissolved in the eluent and applied via a 4-way injection valve to a sample loop (up to 20 ml). Glass columns of C-690 type were used. The exact dimensions are described in the syntheses.

$^1$H NMR Spectroscopy

The measurements were carried out on a Gemini 300 MHz NMR spectrometer from Varian. The calibration of the spectra was carried out from the signal of the residual protons of the deuterated solvent used.

Depth of Cure (DOC)

The depth of cure was determined in accordance with the "Polymerization depth" test according to ISO 4049:2000. For this, the pastes were packed into cylindrical Teflon moulds (diameter 5 mm, height 10 mm) and illuminated from above with a halogen lamp (Translux EC, Heraeus Kulzer) or an LED lamp (Mini LED, Acetone) for 5, 10 or 20 s. Directly after the illuminating, the cured test specimens were taken out and freed from uncured material using a knife. The height of the cured region was determined with a slide gauge and given as depth of cure (DOC) in mm.

Flexural Strength

Test specimens with the dimensions 40±2 mm×2±0.1 mm×2±0.1 mm were prepared using a plastic mould. For this, the respective pastes were light-cured in a light oven (HiLite Power, Heraeus Kulzer). The pastes were first illuminated in the mould for 90 s, subsequently turned over and illuminated again for 90 s.

After removing from the mould, the test specimens were stored in deionized water at 37° C. for 23 h and then at 23° C. for 1 h. Subsequently, the flexural strength (FS) was measured according to ISO 4049:2000 using a universal testing machine (type Z 010/TN2A, Zwick). The measurement was carried out at a constant rate of progression of 0.8 mm/min. The calculation of the FS [MPa] was carried out according to the formula:

$$FS = \frac{3 \times F \times l}{2 \times b \times h^2};$$

with

F=maximum force exerted on the test specimens in newtons; l=distance between the supports with an accuracy of ±0.01 mmm; b=breadth of the test specimens immediately before the test, measured in mm; h=height of the test specimens immediately before the test, measured in mm.

Shear Bond Strength (SBS) on Bovine Enamel and Bovine Dentine

Bovine teeth without pulp (Rocholl) were embedded in a cold polymerizable resin (ViscoVoss GTS with an MEKP MEH hardener, Voss Chemie). Immediately before the experimental procedure, 10 bovine teeth per experimental series were abraded wet on the desired background (enamel or dentine) with sandpaper 120 Grit. A fine grinding then took place with sandpaper of the grade 500 Grit. The tooth material had a flat and smooth surface. The abraded teeth were, until further treatment, kept in deionized water. Holes with a diameter of 3 mm were punched into labels. The tooth to be prepared was taken from the water immediately before treatment and the moisture was removed with oil-free compressed air, overdrying being avoided. The perforated label was stuck so centrally to the surface of the tooth that the hole was available for the adhesion. The adhesives were rubbed on the surface of the tooth for 20 s using a disposable brush and subsequently illuminated for 20 s with an LED lamp (Mini LED, Acetone, blue light, 182 mW/cm$^2$). A two-part Teflon mould (height 3 mm) with a drill hole (diameter 3 mm) was subsequently applied in level fashion to the prepared spot and fixed with metal clamps. The drill hole was packed, free of air bubbles, with the adhesive. Irradiating was then carried out for 40 s with an LED lampe (Mini LED, Acetone). After the hardening, the Teflon mould was removed and projecting residues of the cured adhesive were removed with a scalpel. The test specimens thus prepared were then stored at 37° C. for 1 day in a waterbath. Immediately before the measurement of the shear bond strength, the water bath was allowed to cool to 23° C. inside an hour.

The test specimens were clamped into a shear apparatus according to ISO 10477:2004, for the measurement of the shear bond strength, and the SBS was measured at a progression of 0.5 mm/min using a universal testing machine (type Z 010/TN2A, Zwick). The results were given in the form of an average with a standard deviation. Test specimens, the adhesive bonding of which had already dissolved before the measurement or the adhesive bonding of which was not better than the standardized initial force of 0.01 N, enter into the averaging with a shear bond strength of 0 MPa.

Determination of the Water Solubility

The water solubility was determined in deionized water by UV/visible spectroscopy. The spectra were recorded with a UV/visible spectrometer (Evolution 600, Thermo Scientific) between 200-900 nm. The measurement was carried out in quartz cells (path length 10 mm). The pure solvent deionized water was used for the background spectrum. The background spectrum was subtracted from the spectra of the coinitiators.

Dilute solutions of the different coinitiators with known concentrations were prepared in deionized water. The absorption of the different coinitiators was measured in the absorption maximum (between 290-310 nm) and a linear relationship between the known concentrations and the measured absorptions was determined.

Saturated aqueous solutions of the coinitiators were diluted up to the point that the measured absorption falls in the linear region found above. The concentrations of the coinitiators in the saturated aqueous solutions are determined via the Lambert-Beer law.

The following solubilities in water were determined:

|  | Coinitiator | Solubility [mg/l] |
|---|---|---|
|  | Ethyl 4-dimethylaminobenzoate[1] | 36 |
|  | 2-(n-Butoxy)ethyl 4-dimethylaminobenzoate[1] | 35 |
| EHA | 2-Ethylhexyl 4-dimethylaminobenzoate[1] | 26 |
|  | 4-Dimethylaminobenzonitrile[1] | 278 |
| PEGA | Polyethylene glycol monomethyl ether 4-dimethylaminobenzoate | >766 300 |
|  | 4-Dimethylaminobenzamide | 427 |
|  | 4-Dimethylamino-N-propylbenzamide | 680 |
|  | 4-Dimethylamino-N-(2-methoxyethyl)benzamide | 2670 |

[1]Coinitiator according to the state of the art

EXAMPLE COMPOSITIONS

Example 1

One-piece radically polymerizable light-curable adhesive dental composites were prepared and their bond strength (SBS), depth of cure (DOC) and flexural strength (FS) were measured.

First, resin compositions were prepared from the components given each time in the tables. These resin compositions were used as matrix for the fillers added for the preparation of the pastes. For the preparation of the composite pastes, 60 parts of glass powder and 3 parts of silica were suspended in 37 parts of resin matrix. The preparation was otherwise carried out as described in the methods.

|  | Comparison 1 Composite 3 | Comparison 2 Composite 11 | Comparison 3 Composite 4 | According to the invention Composite 9 | According to the invention Composite 6 |
|---|---|---|---|---|---|
| Resin 55/45* | 64.15 | 64.38 | 79.1 | 64.04 | 78.7 |
| HEMA | 24.95 | 24.76 | 11.99 | 24.63 | 11.93 |
| MPD | 9.98 | 9.91 | 8.04 | 9.86 | 7.95 |
| BHT | 0.05 | 0.05 | — | 0.05 | — |
| CQ | 0.2 | 0.2 | 0.2 | 0.2 | 0.2 |
| EHA | 0.67 | 0.7 | 0.67 | — | — |
| PEGA | — | — | — | 1.22 | 1.22 |
| FS | 131 | — | 148 | — | 136 |
| DOC (5 s) | 7.7 | — | 9.1 | — | 8.7 |
| DOC (10 s) | 9.1 | — | 9.9 | — | 9.8 |
| DOC (20 s) | 10 | — | — | — | — |
| SBS Enamel (SD) | — | 5.95 (2.15) | — | 5.12 (1.5) | — |
| SBS Dentine (SD) | — | 2.34 (1.4) | — | 5 (2.2) | — |

*(Bis-GMA 54.92%; TEGDMA 44.93%; BHT 0.15%)

It is seen, for the photoinitiator CQ, that, with the equimolar replacement of a coinitiator of the state of the art (EHA, Composite 11) by a coinitiator according to the invention (PEGA, Composite 9), which exhibits a higher water solubility, virtually a doubling of the bond strength on dentine is achieved. At the same, good values for the DOC and FS are obtained.

Example 2

|  | Comparison 4 Composite 1 | Comparison 5 Composite 2 | Comparison 6 Composite 12 | According to the invention Composite 10 |
|---|---|---|---|---|
| Resin 55/45* | 64.08 | 64.06 | 64.28 | 63.93 |
| HEMA | 24.93 | 24.92 | 24.73 | 24.59 |
| MPD | 9.97 | 9.97 | 9.89 | 9.84 |
| BHT | 0.05 | 0.05 | 0.05 | 0.05 |
| CQ-10-sulphonic acid | 0.3 | — | — | — |
| CQ-10-sulphonate | — | 0.33 | 0.36 | 0.36 |
| EHA | 0.67 | 0.67 | 0.69 | — |
| PEGA | — | — | — | 1.22 |
| FS | 93 | 102 | — | — |
| DOC (5 s) | 3.8 | 4.4 | — | — |
| DOC (10 s) | 6.3 | 7.2 | — | — |
| DOC (20 s) | 8.7 | 9 | — | — |
| SBS Enamel (SD) | — | — | 3.3 (1.45) | 4.13 (1.56) |
| SBS Dentine (SD) | — | — | 1 (1.66) | 4.68 (2.23) |

*(Bis-GMA 54.92%; TEGDMA 44.93%; BHT 0.15%)

It was surprisingly found, in the equimolar replacement of the photoinitiator CQ by its more hydrophilic derivatives that even with these a sharp improvement in the bond strength on dentine is obtained by a coinitiator according to the invention with a higher water solubility (PEGA, Composite 10); however, the absolute values are not further improved. On the other hand, the combination of CQ-10-sulphonate and EHA leads to a significant worsening of the bonding.

The combination of hydrophilic photoinitiator and hydrophobic coinitiator (C12) had the lowest bond shear strengths, both on enamel and on dentine. The combination of hydrophobic photoinitiator and hydrophilic coinitiator (C9) yielded, on enamel, a comparable shear bond strength to C11. The shear bonding on dentine was, in comparison, significantly higher than with C11. The combination of hydrophilic photoinitiator and hydrophilic coinitiator (C10) yielded, in comparison to C9 and C11, a somewhat lower shear bond strength on enamel. The shear bond strength on dentine was, in comparison, likewise significantly higher than with C11.

It can be seen, from this test series, that a hydrophilic or water-soluble, aromatic, tertiary amine as coinitiator makes possible a clear improvement in the bonding on dentine.

Example 3

|  | According to the invention Composite 5 | According to the invention Composite 6 | According to the invention Composite 7 | According to the invention Composite 8 |
|---|---|---|---|---|
| Resin 55/45* | 79.17 | 78.7 | 78.21 | 77.73 |
| HEMA | 12.01 | 11.93 | 11.86 | 11.79 |
| MPD | 8 | 7.95 | 7.9 | 7.85 |
| CQ | 0.2 | 0.2 | 0.2 | 0.2 |
| PEGA | 0.62 | 1.22 | 1.83 | 2.43 |
| FS | 129 | 136 | 140 | 145 |
| DOC (5 s) | 8.2 | 8.7 | 9 | 9 |
| DOC (10 s) | 9.7 | 9.8 | 9.9 | 9.9 |

*(Bis-GMA 54.92%; TEGDMA 44.93%; BHT 0.15%)

By increasing the proportion of coinitiator according to the invention in the composites according to the invention, the flexural strength can in particular be further improved.

The molar ratio of photoinitiator to coinitiator is listed in the following table:

|  | Composites | | | | |
| --- | --- | --- | --- | --- | --- |
|  | 4 | 5 | 6 | 7 | 8 |
| Molar ratio of photoinitiator to coinitiator | 1:2.03 | 1:1.04 | 1:2.04 | 1:3.06 | 1:4.07 |

The invention claimed is:
1. A dental material, comprising:
   a) at least one monomer comprising at least one radically polymerizable ethylenically unsaturated group and at least one acid group,
   b) at least one monomer not comprising any acid groups and comprising at least one radically polymerizable ethylenically unsaturated group,
   c) at least one photoinitiator,
   d) at least one tertiary aromatic amine as coinitiator, which amine exhibits a benzene ring to which at least one dialkylamine group and at least one additional group are directly bonded,
   characterized in that the additional group is chosen from:
      i. carboxylic acid ester groups comprising at least one polyoxyalkylene group with at least 2 oxyethylene and/or oxypropylene units, and
      ii. amide groups.

2. The dental material as claimed in claim 1, characterized in that the at least one additional group comprises at least one polyoxyalkylene group with from 3 to 20, oxyethylene and/or oxypropylene units.

3. The dental material as claimed in claim 1, characterized in that the tertiary aromatic amine is chosen from the group consisting of:

a)

formula I

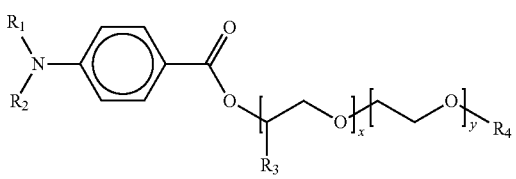

b)

formula II

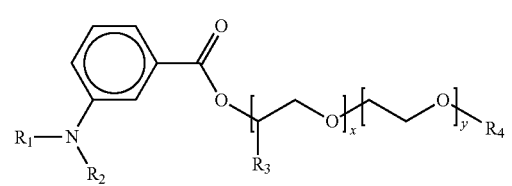

c)

formula III

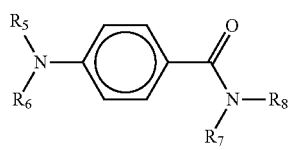

d)

formula IV

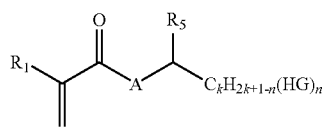

in which in the formulae represented:
$R_1$ and $R_2$ are, independently of one another, $C_1$-$C_5$-alkyl,
$R_3$ is alkyl,
$R_4$ is H or $C_1$-$C_5$-alkyl,
$R_5$ and $R_6$ are, independently of one another, $C_1$-$C_5$-alkyl,
$R_7$ and $R_8$ are, independently of one another, chosen from H, alkyl, alkoxyalkyl and polyalkylene oxide,
$x \geq 0$ and $y > 1$.

4. The dental material as claimed in claim 3, characterized in that the sum of x and y amounts to from 3 to 20.

5. The dental material as claimed in claim 3, characterized in that x is smaller than y.

6. The dental material as claimed in claim 1, characterized in that the water solubility of a coinitiator comprising at least one amide group is at least 0.4 g/l; and that the water solubility of a coinitiator not comprising any amide group is at least 2 g/l.

7. The dental material as claimed in claim 1, characterized in that the content of the coinitiator is from 0.1% to 10% by weight.

8. The dental material as claimed in claim 1, characterized in that the at least one monomer not comprising any acid groups and comprising at least one radically polymerizable ethylenically unsaturated group is chosen from the group consisting of:

b1)

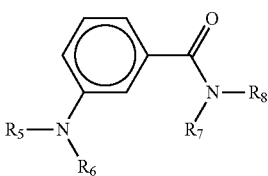

in which, in the formula represented:
$R_1$ is H, methyl or ethyl;
A is O or $NR_3$ with $R_3$=H, methyl;
HG is a hydrophilic group chosen from OH and $(O\text{—}CH_2\text{—}CH_2)_m\text{—}OR_4$;
$R_5$ is H, methyl, ethyl or $C_kH_{2k+1-n}(HG)_n$;
$R_4$ is H or methyl;
k, m, n are natural numbers;
k=1-5;
m=3-20;
n=1-5;
n≤k;
each carbon atom carries at most one hydrophilic group HG;

b2) $(QAE_v)_rC_tH_{2t+2-(r+s)}(HG)_s$
with

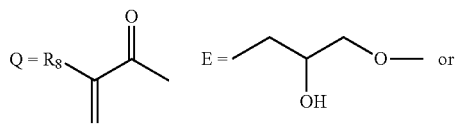

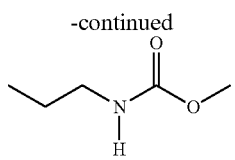

in which, in the formulae represented:
$R_8$ is H, methyl or ethyl;
A is O or $NR_3$, with $R_3$=H, methyl, ethyl or propyl;
HG is OH or $(O-CH_2-CH_2)_m-OR_7$;
$R_7$ is H or methyl;
m, r, s, t, v are natural numbers;
m=3-20;
r=2-4;
s=1-4;
t=2-8;
v=0 or 1; and
b3) $Q-A-E_v-C_2H_2-HG-E_v-A-Q$
with

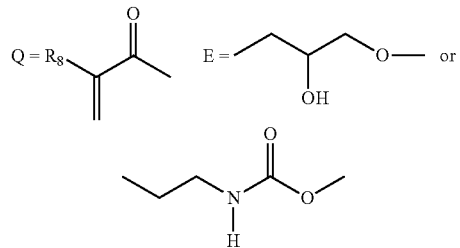

in which, in the formulae represented:
A is 0 or $NR_3$, with $R_3$=H, methyl, ethyl or propyl;
HG is $(O-CH_2-CH_2)_m$;
m=4-20;
v=0 or 1.

9. The dental material as claimed in claim 1, characterized in that it additionally exhibits at least one monomer b4) not comprising any acid groups and comprising at least two radically polymerizable ethylenically unsaturated groups, this at least one monomer b4) not being chosen from the group b1), b2) and b3).

10. The dental material as claimed in claim 8, characterized in that the at least one monomer b1) to b3) exhibits a water solubility of at least 50 g/l.

11. The dental material as claimed in claim 9, characterized in that the at least one monomer b4) exhibits a water solubility of less than 50 g/l.

12. The dental material as claimed in claim 1, for use as light-curing, self-bonding and self-etching radically polymerizable dental restoration material.

13. A method of polymerizing a polymerizable dental material comprising use of a tertiary aromatic amine which exhibits a benzene ring to which at least one dialkylamine group and at least one additional group are directly bonded, the additional group being chosen from:
   i. carboxylic acid ester groups comprising at least one polyoxyalkylene group with at least 2 oxyethylene and/or oxypropylene units, and
   ii. amide groups,
as coinitiator in polymerization of said polymerizable dental material.

14. The dental material as claimed in claim 1, characterized in that the at least one additional group comprises at least one polyoxyalkylene group with from 5 to 17 oxyethylene and/or oxypropylene units.

15. The dental material as claimed in claim 3, characterized in that the sum of x and y amounts to from 5 to 17.

16. The dental material as claimed in claim 3, in which in the formulae represented:
$R_1$ and/or $R_2$ are methyl;
$R_3$ is methyl;
$R_4$ is methyl;
$R_5$ and/or $R_6$ are methyl;
and/or
$R_7$ and/or $R_8$ are polyalkylene oxide with at least two oxyethylene and/or oxypropylene units.

17. The dental material as claimed in claim 6, characterized in that the water solubility of a coinitiator comprising at least one amide group is at least at least 2 g/l.

18. The dental material as claimed in claim 6, characterized in that the water solubility of a coinitiator comprising at least one amide group is at least at least 50 g/l.

19. The dental material as claimed in claim 6, characterized in that the water solubility of a coinitiator not comprising any amide group is at least 50 g/l.

20. The dental material as claimed in claim 1, characterized in that the content of the coinitiator is from 0.5% to 5% by weight.

21. The dental material as claimed in claim 8, characterized in that:
   for b1):
      $R_1$ is H or methyl;
      A is $NR_3$ with $R_3$=H;
      HG=OH;
      $R_5$ is H;
      k=1-2; and/or
      m=5-20,
   for b2):
      $R_8$ is H or methyl;
      A $NR_3$, with $R_3$=H;
      HG is OH;
      m=6-20;
      t=2-6; and/or
      v=0,
   and/or
   for b3):
      A is $NR_3$, with $R_3$=H;
      m=6-20; and/or
      v=0.

* * * * *